US00PP25878P2

(12) United States Plant Patent
Smith

(10) Patent No.: US PP25,878 P2
(45) Date of Patent: Sep. 8, 2015

(54) ***CHRYSANTHEMUM* PLANT NAMED 'CIFZ0013'**

(50) Latin Name: *Chrysanthemum×morifolium*
Varietal Denomination: CIFZ0013

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 42 days.

(21) Appl. No.: 13/999,232

(22) Filed: Jan. 31, 2014

(51) Int. Cl.
*A01H 5/02* (2006.01)

(52) U.S. Cl.
USPC ..... Plt./289

(58) Field of Classification Search
USPC ..... Plt./289
CPC ..... A01H 5/0255; A01H 5/025; A01H 5/02; A01H 5/00
See application file for complete search history.

*Primary Examiner* — Kent L Bell
(74) *Attorney, Agent, or Firm* — Joshua L. Price

(57) ABSTRACT

A new garden type *Chrysanthemum* plant named 'CIFZ0013' particularly distinguished by the medium to large size yellow decorative inflorescences, compact to medium size plant, round mound plant habit, with a natural flowering response of early September.

1 Drawing Sheet

Latin name of the genus and species of the plant claimed: *Chrysanthemum×morifolium.*

Varietal denomination: 'CIFZ0013'.

BACKGROUND OF THE NEW PLANT

The present invention comprises a new *Chrysanthemum*, botanically known as *Chrysanthemum×morifolium*, and hereinafter referred to by the variety name 'CIFZ0013'.

'CIFZ0013' is a product of a planned breeding program. The new cultivar has medium to large size yellow decorative type inflorescences, compact to medium size plant, round mound plant habit, with a natural flowering response of early September.

'CIFZ0013' originated from a hybridization made in February 2008 in a greenhouse in Tenjo, Columbia. The female parent was a commercially available plant designated 'Yoelena', U.S. Plant Pat. No. 20,212, with similar flower color but less disc florets in blackcloth crops, a natural season flower date that is a week later than that of 'CIFZ0013', and somewhat larger plant size under natural flowering conditions.

The male parent of 'CIFZ0013' was the unpatented, proprietary plant designated as 'G0248F6', with red, anemone-type flowers and having a distinctly later natural flowering response. The resultant seed was sown in June 2008 and the young plants were grown outdoors in Alva, Fla. USA.

'CIFZ0013' was selected as one flowering plant within the progeny of the stated cross in late October 2008 in Alva, Fla.

The first act of asexual reproduction of 'CIFZ0013' was accomplished when vegetative cuttings were propagated from the initial selection in a greenhouse in Alva, Fla. in December 2008.

BRIEF SUMMARY OF INVENTION

Horticultural examination of plants grown from cuttings of the plant initiated in December 2008, and continuing thereafter, has demonstrated that the combination of characteristics as herein disclosed for 'CIFZ0013' are firmly fixed and are retained through successive generations of asexual reproduction.

'CIFZ0013' has not been observed under all possible environmental conditions. The phenotype may vary significantly with variations in environment such as temperature, light intensity, and day length.

A Plant Breeder's Right for this cultivar was applied for in Canada on Mar. 8, 2013 (No. 13-7954). 'CIFZ0013' and has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0013' with colors being as true as possible with an illustration of this type.

Figure 1:
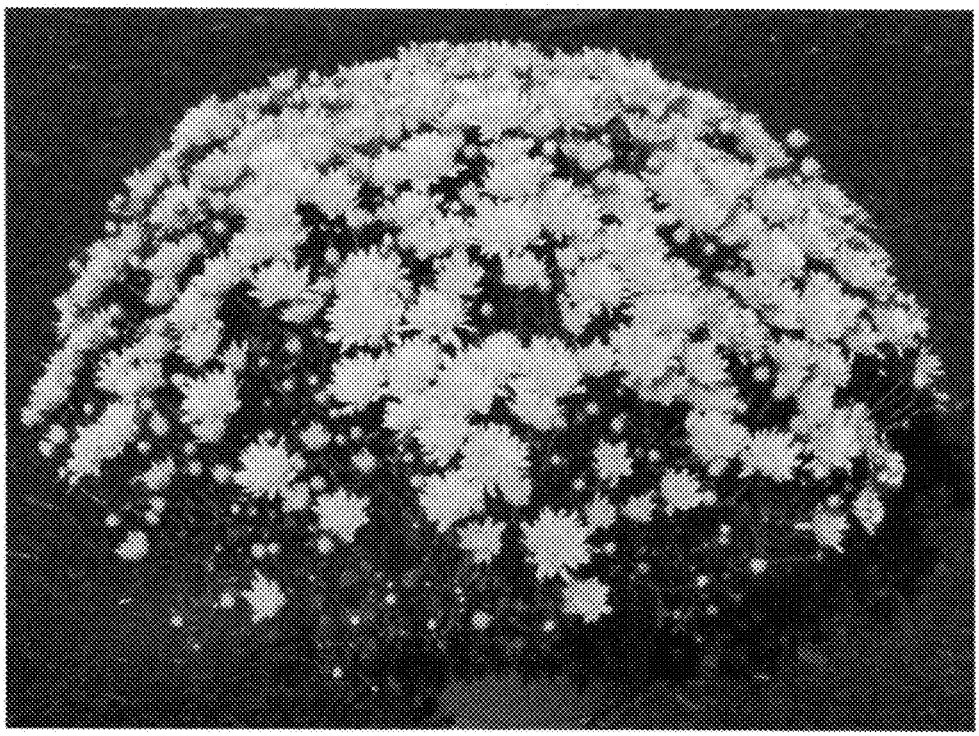
Figure 2:
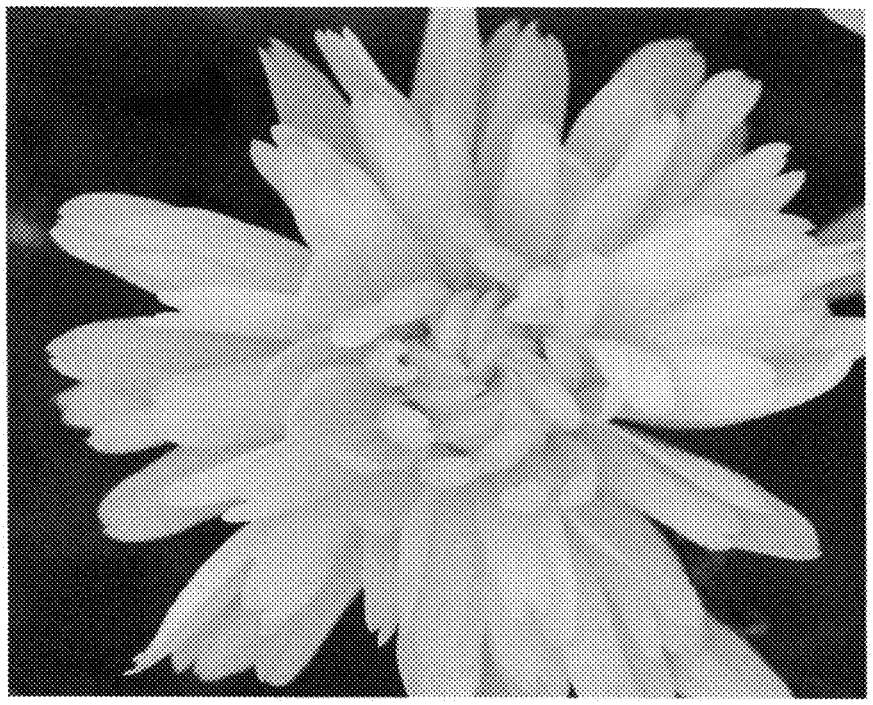

FIG. 1 shows a flowering potted plant of the new variety and FIG. 2 shows a close-up of the flowers.

DETAILED BOTANICAL DESCRIPTION

The plant descriptions and measurements were taken in Gilroy, Calif. in late August 2013 outdoors in natural light. Black-out by black cloth was applied to control day length and to induce early flowering. These plants were grown in 6-inch pots in a greenhouse trial and were about 11 weeks old. These plants were not pinched.

The aforementioned photographs were taken in September 2012 in Monroeville, N.J. These plants were about 12-13 weeks of age. They were grown one plant per nine-inch pot. These plants were not pinched.

Color references are made to The Royal Horticultural Society Colour Chart (R.H.S.) 2001.

TABLE 1

DIFFERENCES BETWEEN THE NEW VARIETY 'CIFZ0013' AND TWO MOST SIMILAR VARIETIES

| | 'CIFZ0013' | 'Yoheidi' (U.S. Plant Pat. No. 13,830) |
|---|---|---|
| Flower type and color: | Same | Similar |
| Plant habit: | Rounder, wider, and less upright | More upright |
| Plant strength: | Stronger | Weaker, splits |
| | 'CIFZ0013' | 'Brilliant Yotiffany' (U.S. Plant Pat. No. 20,219) |
| Flower color: | Dark yellow | Pale yellow |
| Plant size: | Larger | Smaller |
| Plant strength: | Stronger plant | Weaker, splits |

Plant:

*Form, growth and habit.*—Herbaceous garden-type, stems upright and outwardly spreading, freely branching, strong and moderately vigorous growth habit.

*Plant height.*—14-16 cm.

*Plant height* (*inflorescence included*).—20-22 cm.

*Plant width.*—42-45 cm.

Roots:

*Number of days to initiate roots.*—About 4-6 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature, leaf color, upper surface.*—RHS 147A.

*Immature, leaf color, lower surface.*—RHS 146A.

*Mature, leaf color, upper surface.*—RHS 147A.

*Mature, leaf color, lower surface.*—RHS 146A.

*Length.*—4.5-5.2 cm.

*Width.*—2.9-3.3 cm.

*Shape.*—Ovate.

*Base shape.*—Attenuate.

*Apex shape.*—Rounded to obtuse.

*Margin.*—3 main lobes, and irregularly serrulate.

*Texture, upper surface.*—Bifid hair.

*Texture, lower surface.*—Bifid hair.

*Color of veins, upper surface.*—RHS 144B.

*Color of veins, lower surface.*—RHS 144B.

*Pattern of veining.*—Palmate.

*Petiole color.*—RHS 144B.

*Length.*—0.9-1.1 cm.

*Diameter.*—0.15-0.2 cm.

*Texture.*—Bifid hair.

Stem:

*Quantity of main branches per plant.*—8-10.

*Color of stem.*—From RHS 137A to 137B.

*Length of stem.*—About 10-13 cm.

*Diameter.*—0.25-0.30 cm.

*Length of internodes.*—0.75-1.00 cm.

*Texture.*—Covered with bifid hair.

*Color of peduncle.*—RHS 138B.

*Length of peduncle.*—5.5-7.1 cm.

*Peduncle diameter.*—0.15 cm.

*Texture.*—Covered with bifid hair.

Inflorescence:

*Type.*—Compositae, solitary, decorative-type inflorescences borne terminally above foliage, ray florets arranged on a capitulum.

*Quantity of short days to flowering* (*response time*).—6.5 weeks.

*Natural season flowering.*—Early September.

*Quantity of inflorescences per plant.*—55-60, plus many additional buds in various stages of development.

*Lastingness of individual blooms on the plant.*—About 6 weeks from the first color depending on conditions.

*Fragrance.*—Slightly spicy.

Bud (just when opening/showing color):

*Color.*—RHS 7A.

*Length.*—1.0-1.7 cm.

*Width.*—1.0-1.3 cm.

*Shape.*—Oblate.

Immature inflorescence:

*Diameter.*—5.5-5.8 cm.

*Color of ray florets, upper surface.*—RHS 7A.

*Color of ray florets, lower surface.*—RHS 7B.

Mature inflorescence:

*Diameter.*—6.0-6.6 cm.

*Depth.*—2.0-2.5 cm.

*Total diameter of disc.*—Very small, not visible as covered by the many rays.

*Receptacle color.*—RHS 145B.

*Receptacle height.*—0.4 cm.

*Receptacle diameter.*—0.25 cm.

Ray florets:

*Average quantity of florets.*—About 70-100 in many whorls.

*Color of florets, upper surface.*—RHS 6A.

*Color of florets, lower surface.*—RHS 6A.

*Length.*—Approximately 2.5-3.0 cm.

*Width.*—0.5-0.65 cm.

*Shape.*—Oblong to elliptical.

*Apex shape.*—Most often emarginate or praemorse.

*Base shape.*—Cuneate.

*Margin.*—Entire.

*Texture, upper surface.*—Papillate.

*Texture, lower surface.*—Papillate.

Disc florets:

*Average quantity of florets.*—30-35.

*Color of florets.*—RHS 1B, or slightly more greenish.

*Length.*—0.2-0.35 cm.

*Width.*—0.1 cm.

*Shape.*—Tubular, elongated.

*Apex shape.*—Acute, 5 pointed.

Phyllaries:

*Quantity.*—Approximately 20.

*Color, upper surface.*—RHS 137C.

*Color, lower surface.*—RHS 137B.

*Length.*—0.6-0.7 cm.

*Width.*—0.15-0.2 cm.

*Shape.*—Lanceolate.

*Apex shape.*—Acute.

*Base.*—Fused.

*Margins.*—Entire, some with papery edges.

*Texture, upper surface.*—Glabrous.

*Texture, lower surface.*—Bifid hairs.

Reproductive organs:

*Pistil.*—1, found on both types of florets.

*Length.*—0.5-0.6 cm.

*Style color.*—RHS 1C.

*Style length.*—0.35-0.40 cm.
*Stigma color.*—RHS 7D.
*Stigma shape.*—Bi-lobed.
*Ovary color.*—RHS 145C.
*Ovary length.*—0.15 cm.
*Ovary width.*—0.1 cm.
*Stamens.*—4, found on only on the disc florets.
*Color of filaments.*—RHS 155C.
*Length filaments.*—0.15 cm.
*Anther color.*—RHS 6A.
*Anther length.*—0.1 cm.
*Anther shape.*—Oblong.
*Color of pollen.*—RHS 15C.
*Pollen amount.*—Sparse.
*Fertility/seed set.*—Has not been determined to date.
*Disease/pest resistance.*—Has not been determined to date.

What is claimed is:

1. A new and distinct variety of *Chrysanthemum* plant named 'CIFZ0013' substantially as illustrated and described herein.

* * * * *